United States Patent [19]

Swanson

[11] Patent Number: 5,759,158
[45] Date of Patent: Jun. 2, 1998

[54] SYSTEMS AND METHODS FOR CONDUCTING ELECTROPHYSIOLOGICAL TESTING USING HIGH-VOLTAGE ENERGY PULSES TO STUN HEART TISSUE

[75] Inventor: David K. Swanson, Mountain View, Calif.

[73] Assignee: E.P. Technologies, Inc., San Jose, Calif.

[21] Appl. No.: 914,860

[22] Filed: Aug. 19, 1997

Related U.S. Application Data

[63] Continuation of Ser. No. 791,625, Jan. 31, 1997, abandoned, which is a continuation of Ser. No. 508,750, Jul. 28, 1995, abandoned.

[51] Int. Cl.⁶ .................................................. A61B 5/02
[52] U.S. Cl. ...................................................... 600/508
[58] Field of Search ............................ 128/642, 697, 128/695; 606/33, 34, 41, 42; 607/7, 9, 11, 25, 128

[56] References Cited

U.S. PATENT DOCUMENTS

| | | | |
|---|---|---|---|
| 4,056,105 | 11/1977 | Ravas . | |
| 4,660,571 | 4/1987 | Hess et al. | 128/642 |
| 4,768,512 | 9/1988 | Imran | 607/5 |
| 4,785,815 | 11/1988 | Cohen | 128/642 |
| 4,869,248 | 9/1989 | Narula | 128/642 |
| 4,953,564 | 9/1990 | Berthelsen | 607/128 |
| 5,088,489 | 2/1992 | Lerman | 607/7 |
| 5,156,151 | 10/1992 | Imran | 128/642 |
| 5,222,501 | 6/1993 | Ideker et al. | 128/662.06 |
| 5,246,438 | 9/1993 | Langberg | 128/642 |
| 5,282,840 | 2/1994 | Hudrlik | 607/28 |
| 5,323,781 | 6/1994 | Ideker et al. | 128/662.06 |
| 5,324,284 | 6/1994 | Imran | 128/642 |
| 5,431,649 | 7/1995 | Mulier et al. | 128/642 |
| 5,433,798 | 7/1995 | Desai | 128/642 |
| 5,450,846 | 9/1995 | Goldreyer | 128/642 |
| 5,454,370 | 10/1995 | Avitall | 128/642 |

*Primary Examiner*—William F. Karn
*Assistant Examiner*—George R. Evanisko
*Attorney, Agent, or Firm*—Oppenheimer Poms Smith

[57] ABSTRACT

Systems and methods for diagnosing and treating cardiac disorders transmit an electrical energy pulse that temporarily stuns a zone of myocardial tissue, temporarily rendering it electrically unresponsive. The systems and methods sense an electrophysiological effect due to the transmitted pulse. The systems and methods alter an electrophysiological property of myocardial tissue in or near the zone based, at least in part, upon the sensed electrophysiological effect. The alteration of the electrophysiological property can be accomplished, for example, by tissue ablation or by the administration of medication. In a preferred implementation, radio frequency energy is used to both temporarily stun myocardial tissue and to ablate myocardial tissue through a common electrode.

58 Claims, 8 Drawing Sheets

SYSTEMS AND METHODS FOR CONDUCTING ELECTROPHYSIOLOGICAL TESTING USING HIGH-VOLTAGE ENERGY PULSES TO STUN HEART TISSUE

This application is a continuation of application Ser. No. 08/791,625 abandoned, filed Jan. 31, 1997, which is itself a continuation of application Ser. No. 08/508,750, filed Jul. 28, 1995, now abandoned.

FIELD OF THE INVENTION

The invention generally relates to systems and methods for diagnosing or treating cardiac conditions. In a more particular sense, the invention relates to systems and methods for locating potential efficacious sites for ablating heart tissue to treat arrhythmia.

BACKGROUND OF THE INVENTION

Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract.

This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates errant, circular propagation patterns, called "circus motion." The circus motion also disrupts the normal depolarization patterns, thereby disrupting the normal contraction of heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT).

In treating arrhythmias, it is essential that the location of the sources of the aberrant pathways (call foci) be located. Once located, the tissue in the foci can be destroyed, or ablated, by heat, chemicals, or other means. Ablation can remove the aberrant conductive pathway, restoring normal myocardial contraction.

Today, physicians examine the propagation of electrical impulses in heart tissue to locate aberrant conductive pathways. The techniques used to analyze these pathways, commonly called "mapping," identify regions in the heart tissue, called foci, which can be ablated to treat the arrhythmia.

One form of conventional cardiac tissue mapping techniques uses multiple electrodes positioned in contact with epicardial heart tissue to obtain multiple electrograms. The physician stimulates myocardial tissue by introducing pacing signals and visually observes the morphologies of the electrograms recorded during pacing, which this Specification will refer to as "paced electrograms." The physician visually compares the patterns of paced electrograms to those previously recorded during an arrhythmia episode to locate tissue regions appropriate for ablation. These conventional techniques require invasive open heart surgical techniques to position the electrodes on the epicardial surface of the heart.

Conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct foci identification rates (CIR) cannot be achieved with current multi-electrode mapping technologies.

In treating VT using conventional open-heart procedures, the physician may temporarily render a localized region of myocardial tissue electrically unresponsive during an induced or spontaneous VT episode. This technique, called "stunning," is accomplished by cooling the tissue. If stunning the localize region interrupts an ongoing VT, or suppresses a subsequent attempt to induce VT, the physician ablates the localized tissue region. However, in conventional practice, cooling a significant volume of tissue to achieve a consistent stunning effect is clinically difficult to achieve.

Another form of conventional cardiac tissue mapping technique, called pace mapping, uses a roving electrode in a heart chamber for pacing the heart at various endocardial locations. In searching for the VT foci, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

These techniques are complicated and time consuming. They require repeated manipulation and movement of the pacing electrodes. At the same time, they require the physician to visually assimilate and interpret the electrocardiograms.

There thus remains a real need for systems and procedures that simplify the location of appropriate arrhythmogenic foci, and, in particular, without costly and invasive open-heart surgery.

SUMMARY OF THE INVENTION

A principal objective of the invention is to provide improved systems and methods to examine heart tissue morphology quickly and accurately.

One aspect of the invention provides systems and methods for conducting diagnostic electrophysiological testing of myocardial tissue. The systems and methods transmit an electrical energy pulse that temporarily renders a zone of myocardial tissue electrically unresponsive. The systems and methods sense an electrophysiological effect due to the transmitted pulse. Based upon sensing the electrophysiological effect caused by the transmitted pulse, the physician can diagnose cardiac events. For example, by temporarily rendering localized zones of myocardial tissue electrically unresponsive, the physician can locate potential pacemaker sites or slow conduction zones associated with arrhythmia. Using the same process, the physician can selectively alter conduction properties in the localized zone, without changing electrophysiological properties of tissue outside the zone.

In a preferred embodiment, the systems and methods alter an electrophysiological property of myocardial tissue in or near the diagnosed zone based, at least in part, upon the sensed electrophysiological effect. The electrophysiological property can be altered, for example, by ablating myocardial tissue in or near the zone or by administering drugs to mediate the diagnosed cardiac disorder.

Another aspect of the invention provides systems and methods for ablating myocardial tissue. The systems and methods transmit an electrical energy pulse that temporarily renders myocardial tissue electrically unresponsive. The systems and methods sense an electrophysiological effect due to the transmitted pulse. The systems and methods ablate the myocardial tissue when the sensed electrophysiological effect meets preestablished criteria.

In a preferred embodiment, the systems and methods use radio frequency energy to both temporarily render myocardial tissue electrically unresponsive as well as ablate the tissue, should the established criteria be met. In this preferred embodiment, the same electrode is used to transmit the radio frequency energy, which, in one mode, temporarily renders the tissue electrically unresponsive and which, in a second mode, ablates the tissue.

Another aspect of the invention provides an electrical energy generating device. The device comprises a first element that, when activated, generates for transmission by an electrode coupled to the device an electrical energy pulse that temporarily renders myocardial tissue electrically unresponsive. The device also comprises a second element that, when activated, generates for transmission by an electrode coupled to the device electrical energy to ablate myocardial tissue. A switch selects for activation either the first element or the second element.

In a preferred embodiment, both first and second elements of the device generate radio frequency energy.

Other features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
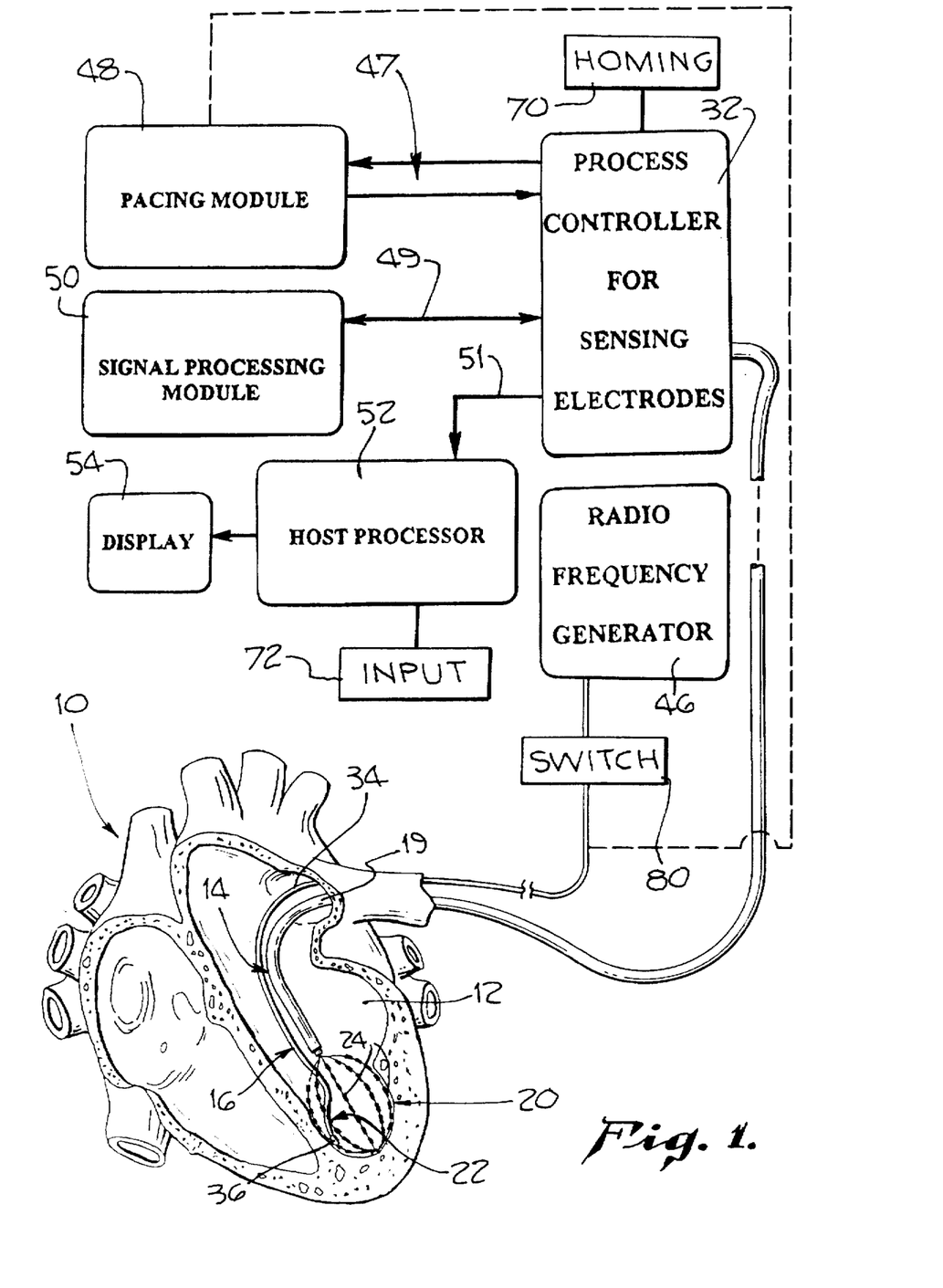
FIG. 1 is a diagrammatic view of a system, which embodies the features of the invention, for accessing a targeted tissue region in the body for diagnostic or therapeutic purposes.

FIG. 1 shows the system 10 analyzing endocardial electrical events, using catheter-based, vascular access techniques. The system 10 examines the depolarization of heart tissue that is subject to an arrhythmia. The system 10 locates a potential tissue site for ablation.

The system 10 includes a mapping probe 14 and a multi-purpose stunning-ablation probe 16. In FIG. 1, each is separately introduced into the selected heart region 12 through a vein or artery (typically the femoral vein or artery) through suitable percutaneous access. Alternatively, the mapping probe 14 and multi-purpose stunning-ablation probe 16 can be assembled in an integrated structure for simultaneous introduction and deployment in the heart region 12.

Further details of the deployment and structures of the probes 14 and 16 are set forth in pending U.S. patent application Ser. No. 08/033,641, filed Mar. 16, 1993, entitled "Systems and Methods Using Guide Sheaths for Introducing, Deploying, and Stabilizing Cardiac Mapping and Ablation Probes."

I. THE MAPPING PROBE

The mapping probe 14 has a flexible catheter body 18. The distal end of the catheter body 18 carries a three dimensional multiple-electrode structure 20. In the illustrated embodiment, the structure 20 takes the form of a basket defining an open interior space 22 (see FIG. 2). It should be appreciated that other three dimensional structures could be used.

Figure 2:
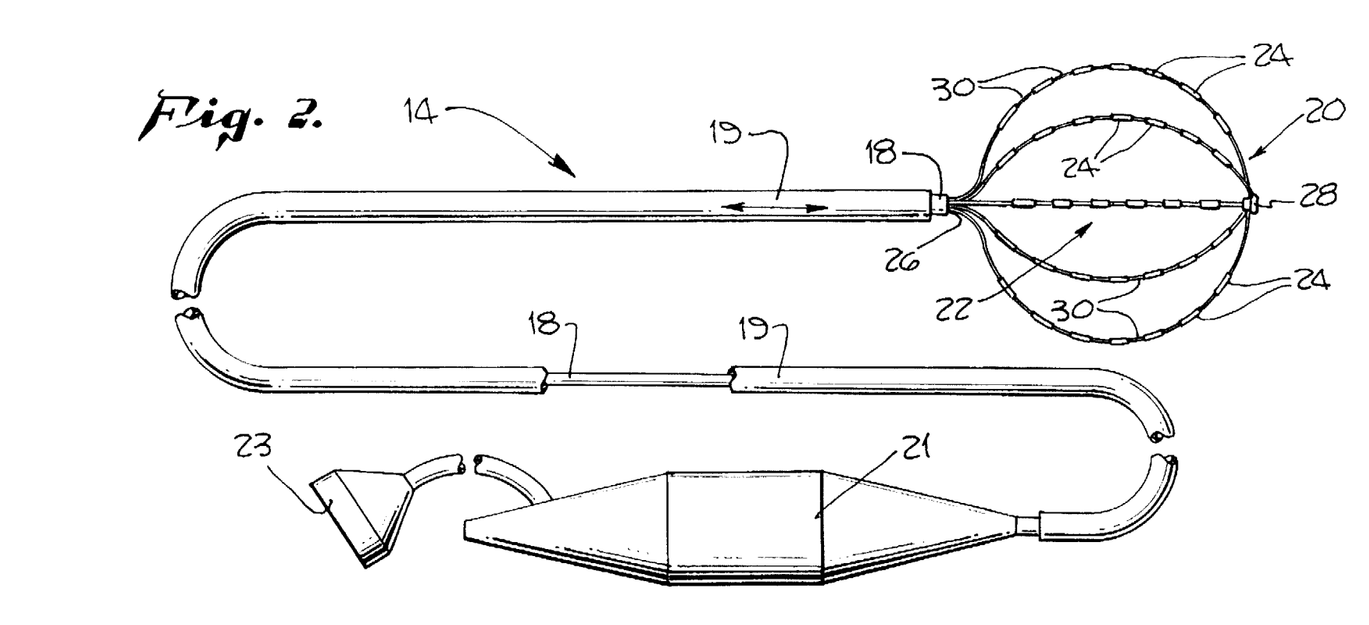
FIG. 2 is an enlarged perspective view of a multiple-electrode structure used in association with the system shown in FIG. 1.

As FIG. 2 shows, the illustrated basket structure 20 comprises a base member 26 and an end cap 28. Generally flexible splines 30 extend in a circumferentially spaced relationship between the base member 26 and the end cap 28.

The splines 30 are preferably made of a resilient, biologically inert material, like Nitinol metal or silicone rubber. The splines 30 are connected between the base member 26 and the end cap 28 in a resilient, pretensed, radially expanded condition, to bend and conform to the endocardial tissue surface they contact. In the illustrated embodiment (see FIG. 2), eight splines 30 form the basket structure 20. Additional or fewer splines 30 could be used.

The splines 30 carry an array of electrodes 24. In the illustrated embodiment, each spline 30 carries eight electrodes 24. Of course, additional or fewer electrodes 24 can be used.

A slidable sheath 19 is movable along the axis of the catheter body 18 (shown by arrows in FIG. 2). Moving the sheath 19 forward causes it to move over the basket structure 20, collapsing it into a compact, low profile condition for introducing into the heart region 12. Moving the sheath 19 rearward frees the basket structure 20, allowing it to spring open and assume the pretensed, radially expanded position shown in FIG. 2. The electrodes are urged into contact against the surrounding heart tissue.

Further details of the basket structure are disclosed in pending U.S. patent application Ser. No. 08/206,414, filed Mar. 4, 1994, entitled "Multiple Electrode Support Structures."

In use, the electrodes 24 sense electrical events in myocardial tissue for the creation of electrograms. The electrodes 24 are electrically coupled to a process controller 32 (see FIG. 1). A signal wire (not shown) is electrically coupled to each electrode 24. The wires extend through the body 18 of the probe 14 into a handle 21 (see FIG. 2), in which they are coupled to an external multiple pin connector 23. The connector 23 electrically couples the electrodes to the process controller 32.

Alternatively, multiple electrode structures can be located epicardially using a set of catheters individually introduced through the coronary vasculature (e.g., retrograde through the aorta or coronary sinus), as disclosed in PCT/US94/01055 entitled "Multiple Intravascular Sensing Devices for Electrical Activity."

II. THE PROCESS CONTROLLER

In the illustrated and preferred embodiment, the process controller 32 induces electrical events in heart tissue by transmitting pacing signals into heart tissue. The process controller 32 senses these electrical events in heart tissue to process and analyze them to locate a potential ablation site.

More particularly (see FIG. 1), the process controller 32 is electrically coupled by a bus 47 to a pacing module 48, which paces the heart sequentially through individual or pairs of electrodes to induce depolarization. Details of the process controller 32 and pacing module 48 are described in copending U.S. patent application Ser. No. 08/188,316, filed Jan. 28, 1994, and entitled "Systems and Methods for Deriving Electrical Characteristics of Cardiac Tissue for Output in Iso-Characteristic Displays." The process controller 32 is also electrically coupled by a bus 49 to a signal processing module 50. The processing module 50 processes cardiac signals into electrograms. A Model TMS 320C31 processor available from Spectrum Signal Processing, Inc. can be used for this purpose.

The process controller 32 is further electrically coupled by a bus 51 to a host processor 52, which processes the input from the electrogram processing module 50. The output of the host processor 32 can be selectively displayed for viewing by the physician on an associated display device 54. The host processor 52 can comprise a 486-type microprocessor.

According to the invention, the process controller 32 operates in two functional modes, called the sampling mode and the matching mode.

A. The Sampling Mode

In the sampling mode, the physician deploys the basket structure 20 in the desired heart region 12. To assure adequate contact is made in the desired region 12, the physician may have to collapse the basket structure 20, rotate it, and then free the basket structure 20. The degree of contact can be sensed by the process controller 32 in various ways. For example, the process controller 32 can condition the pacing module 48 to emit pacing signals through a selected electrode 24 or pair of electrodes 24. The process controller 32 conditions the electrodes 24 and processing module 50 to detect electrograms sensed by a desired number of the electrodes 24. The processing module can also ascertain the desired degree of contact by measuring tissue impedance, as described in copending patent application Ser. No. 08/221,347, filed Mar. 31, 1994, and entitled "Systems and Methods for Positioning Multiple Electrode Structures in Electrical Contact with the Myocardium."

Once the basket structure 20 is properly positioned, the process controller 32 conditions the electrodes 24 and signal processing module 50 to record electrograms during a selected cardiac event having a known diagnosis. In the sampling mode, the process controller 32 typically must condition the pacing module 48 to pace the heart until the desired cardiac event is induced. Of course, if the patient spontaneously experiences the cardiac event while the structure 20 is positioned, then paced-induction is not required.

In the illustrated and preferred embodiment, the selected event comprises an arrhythmia that the physician seeks to treat, for example, ventricular tachycardia (VT), or atrial tachycardia (AT), or atrial fibrillation (AF).

Figure 4A:
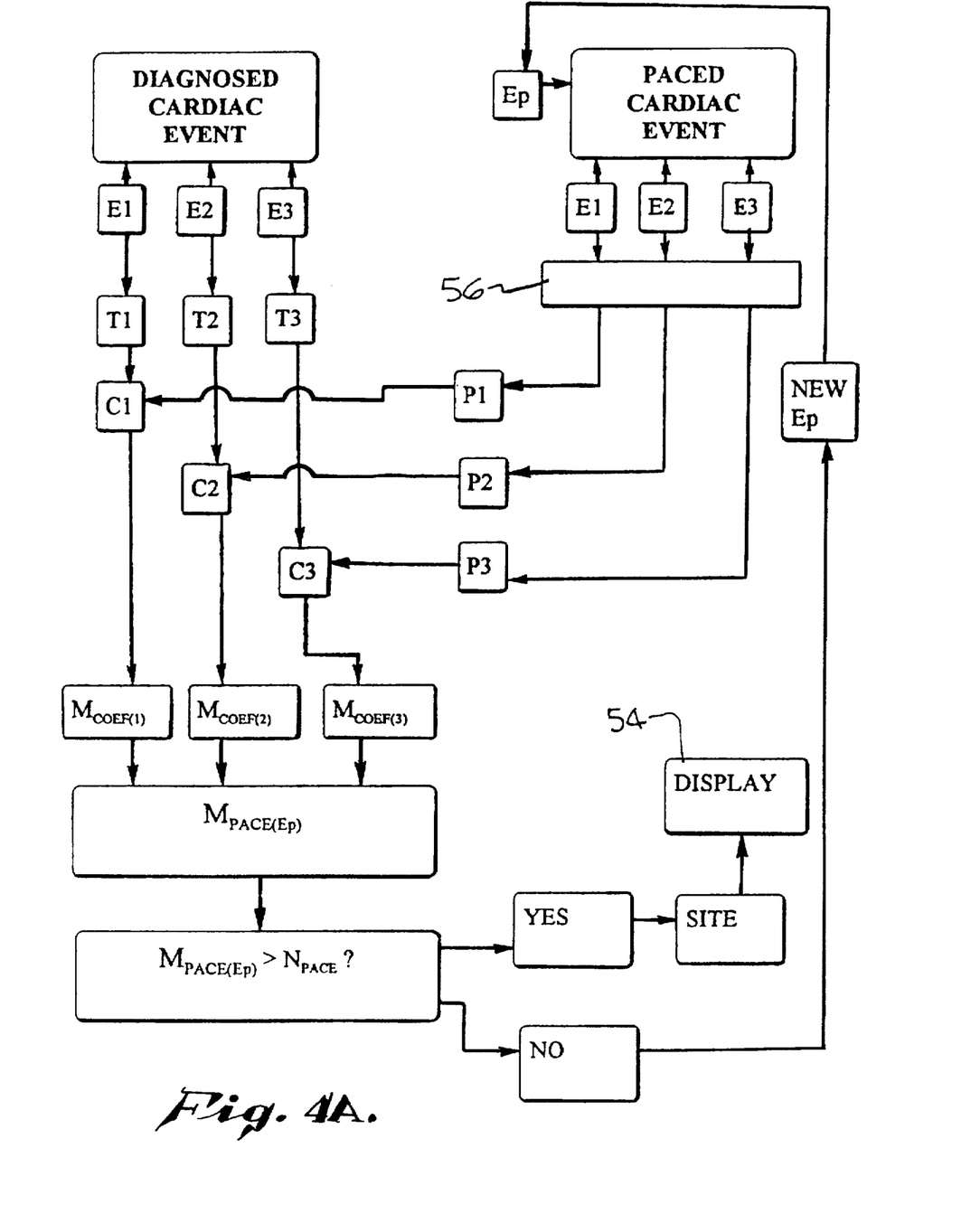
FIG. 4A is a diagrammatic view of the process controller shown in FIG. 1, which locates by electrogram matching a site appropriate for ablation.

As FIG. 4A shows, during the sampling mode, the signal processing module 50 processes the electrogram morphologies obtained from each electrode during the known cardiac event (designated for the purpose of illustration as E1 to E3 in FIG. 4A). The electrograms may be recorded unipolar (between an electrode 24 and a reference electrode, not shown) or bipolar (between electrodes 24 on the structure 20).

The host processor 52 creates a digital, event-specific template for the morphology sensed at each electrode (designated for the purpose of illustration as T1 to T3 in FIG. 4A). The process controller 32 creates templates of selected electrogram morphologies by any conventional method, e.g., by having the physician manually select representative electrogram morphologies.

The event-specific templates T1 to T3 for each electrode E1 to E3 can be based upon electrogram morphology from one heart beat or a specified number of heart beats. The event-specific template T1 to T3 for each electrode E1 to E3 can be created by, for example, having the physician manually select representative electrogram morphologies.

If the arrhythmia event is not polymorphic, the template preferably comprises one heart beat and is updated beat by beat. Also preferably, though not essential, the starting point of the template should coincide with the beginning of the depolarization and extend one beat from that point. However, if the arrhythmia event under study is polymorphic, it may be necessary to extend the template over several beats. For example, in bigeminy cases, the template should preferably extend over two beats.

The host processor 52 retains the set of event-specific templates T1 to T3 in memory. The processor 52 can, for an individual patient, retain sets of event-specific templates for different cardiac events. For example, a patient may undergo different VT episodes, each with a different morphology. The processor 52 can store templates for each VT episode for analysis according to the invention. The templates can be downloaded to external disk memory for off-line matching at a subsequent time. Templates can also be generated based upon mathematical modeling or empirical data and stored for later matching for diagnostic purposes.

At the end of the sampling mode, the process controller 32 typically must condition the pacing module 48 to pace terminate the cardiac event, or the physician may apply a shock to restore normal sinus rhythm.

B. The Matching Mode

The matching mode is conducted without altering the position of the multiple electrode structure 20 in the heart region 12, so that the electrodes 24 occupy the same position during the matching mode as they did during the sampling mode.

In the matching mode, the process controller 32 operates the pacing module 48 to apply pacing signals sequentially to each of the individual electrodes. The pacing electrode is designated Ep in FIG. 4A.

The pacing signal induces depolarization, emanating at the location of the pacing electrode Ep. The process controller 32 operates the signal processing module 50 to process the resulting paced electrogram morphologies sensed at each electrode (again designated E1 to E3 for the purpose of illustration in FIG. 4A) during pacing by the selected individual electrode Ep. The processed paced electrograms are designated P1 to P3 in FIG. 4A.

The paced morphology P1 to P3 at each electrode can be from one heart beat or a specified number of heart beats, provided that the length of the morphologies P1 to P3 is not shorter than the length of the event-specific templates T1 to T3 for the same electrodes E1 to E3 obtained during the sampling mode.

Different conventional pacing techniques can be used to obtain the paced morphologies P1 to P3. For example, conventional pace mapping can be used, during which the pace rate is near the arrhythmia rate, but arrhythmia is not induced.

Conventional entrainment or reset pacing is the preferred technique. During entrainment pacing, the pacing rate is slightly higher than and the period slightly lower than that observed during the arrhythmia event, thereby increasing the rate of the induced arrhythmia event. Further details of entrainment pacing are found in Almendral et al., "Entrainment of Ventricular Tachycardia: Explanation for Surface Electrocardiographic Phenomena by Analysis of Electrograms Recorded Within the Tachycardia Circuit," *Circulation*, vol. 77, No. 3, March 1988, pages 569 to 580, which is incorporated herein by reference.

Regardless of the particular pacing technique used, the pacing stimulus may be monophasic, biphasic, or triphasic.

Pacing artifacts in the pacing electrograms may be eliminated by conventional techniques to better discern the initial point of depolarization. The process controller 32 may also remove the pacing artifact for this purpose without otherwise altering the morphology of the electrogram using nonlinear or adaptive filters, as described in greater detail in copending Panescu et al. U.S. patent application Ser. No. 08/390,587, filed Feb. 17, 1995, entitled "Systems and Methods for Filtering Signals Derived from Biological Events."

In the matching mode, while pacing at an individual one of the electrodes Ep, the host processor 52 compares the paced morphology P1 to P3 obtained at each electrode E1 to E3 to the stored event-specific template T1 to T3 for the same electrode E1 to E3. The comparisons (which are designated C1 to C3 in FIG. 4A) can be performed by using matched filtering or correlation functions.

Alternatively, the paced morphologies P1 to P3 can be retained in memory or downloaded to external disk memory for matching at a later time. To accommodate off-line processing, the host processor 52 preferably includes an input module 72 (see FIG. 1) for uploading pregenerated templates and/or paced morphologies recorded at an earlier time. The input module 72 allows templates and paced morphologies to be matched off-line by the host processor 52, without requiring the real time presence of the patient. Alternatively, recorded paced morphologies can be matched in real time using templates generated earlier. The pregenerated templates can represent "typical" biopotential events based upon either real, empirical data, or mathematical models for diagnostic purposes, or reflect earlier biopotential events recorded for the same patient or for a patient having the same or similar prognosis.

For each pacing electrode Ep(j), the host processor 52 generates a matching coefficient $M_{COEF(i)}$ for each electrode E(i) from the comparison C(i) of the pacing morphology P(i) to the template morphology T(i) for the same electrode E(i). Preferably, both j and i=1 to n, where n is the total number of electrodes on the three dimensional structure (which, for the purpose of illustration in FIG. 4A, is 3).

The value of the matching coefficient $M_{COEF(i)}$ is indicative for that electrode E(i) how alike the pacing morphology P(i) is to the event-specific template T(i) for that electrode E(i). The value of $M_{COEF(i)}$ for each electrode E(i) varies as the location of the pacing electrode Ep(j) changes. Generally speaking, the value of the matching coefficient $M_{COEF(i)}$ for a given electrode E(i) increases in relation to the closeness of the pacing electrode Ep(j) to the arrhythmogenic foci. In the illustrated and preferred embodiment (as FIG. 4A shows), while pacing at an individual one of the electrodes Ep(j), the host processor 52 generates from the matching coefficients $M_{COEF(i)}$ for each electrode E(i) an overall matching factor $M_{PACE(j)}$ for the pacing electrode Ep(j). The value of the overall matching factor $M_{PACE(j)}$ for the pacing electrode Ep(j) is indicative of how alike the overall propagation pattern observed during pacing at the electrode Ep(j) is to the overall propagation pattern recorded on the associated event-specific templates.

The process controller 32 operates the pacing module 48 to apply a pacing signal sequentially to each electrode Ep(j) and processes and compares the resulting electrogram morphologies at each electrode E(i) (including Ep(j)) to the event-specific templates, obtaining the matching coefficients $M_{COEF(i)}$ for each electrode E(i) and an overall matching factor $M_{PACE(j)}$ for the pacing electrode Ep(j), and so on, until every electrode E(i) serves as a pacing electrode Ep(j).

$M_{PACE(j)}$ for each pacing electrode can be derived from associated matching coefficients $M_{COEF(i)}$ in various ways.

For example, various conventional averaging techniques can be used. For example, $M_{PACE(j)}$ can be computed as a first order average (arithmetic mean) of $M_{COEF(i)}$ as follows:

$$M_{PACE(j)} = \frac{\Sigma M_{COEF(i)}}{n}$$

where i=1 to n; or as a weighted arithmetic mean, as follows:

$$M_{PACE(j)} = \Sigma W(i) M_{COEF(i)}$$

where i=1 to n; $\Sigma W(i)=1$. If W(i)=1/n, for each i, then the arithmetic mean is obtained.

Generally speaking, the value of the overall matching factor $M_{PACE(j)}$ increases in relation to the proximity of the particular pacing electrode Ep(j) to a potential ablation site.

The matching of pacing morphologies P(i) to template morphologies T(i) to create the matching coefficient $M_{COEF(i)}$ and the overall matching factor $M_{PACE(i)}$ can be accomplished in various ways. The host processor 52 can employ pattern matching; symmetry matching; matched filtering; cross correlation; or norm of the difference techniques.

1. Pattern Matching

Figure 5:
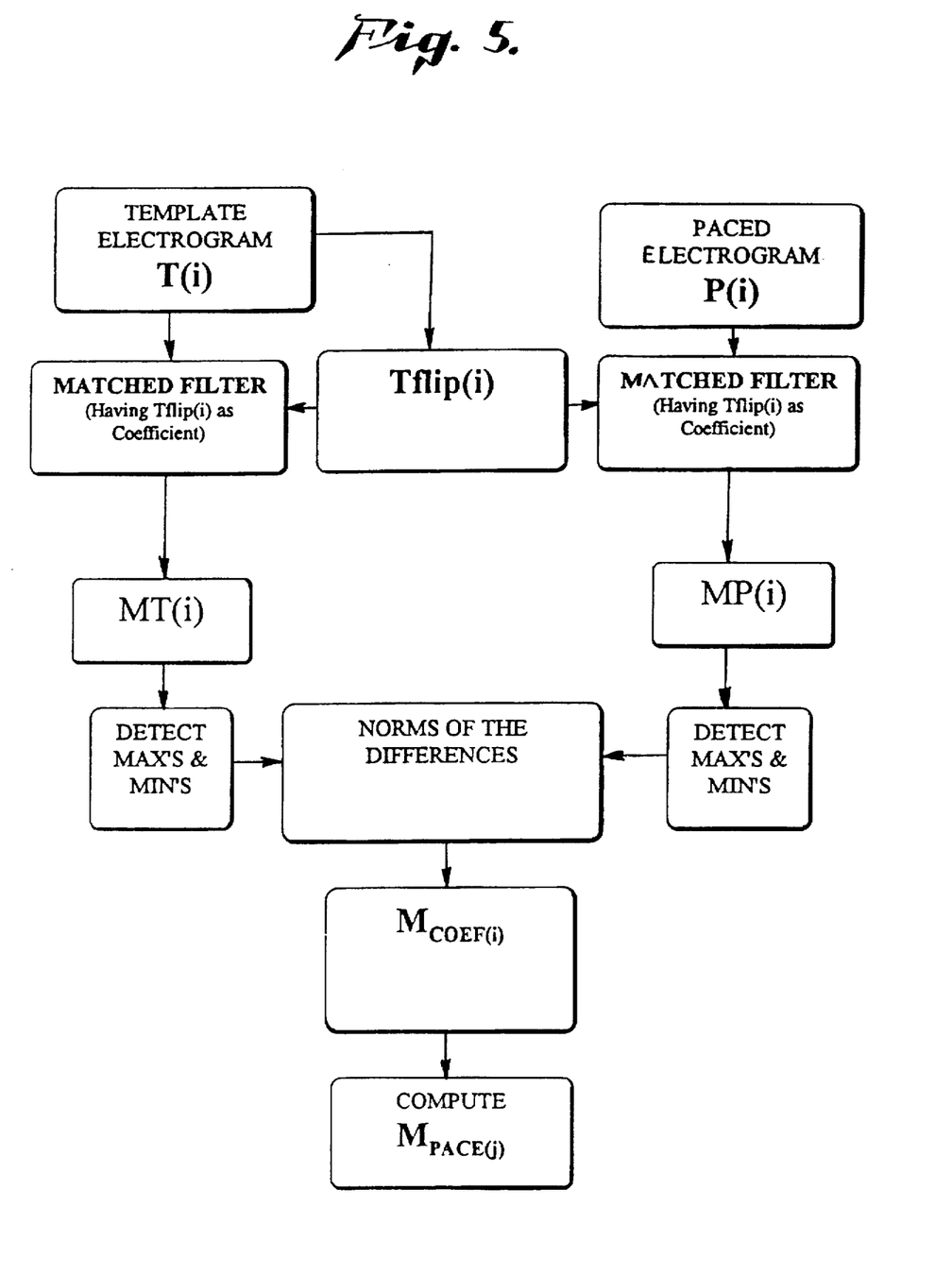
FIG. 5 is a flow chart showing a pattern matching technique that the process controller shown in FIG. 4A can employ for matching electrograms according to the invention.
Figure 6A:
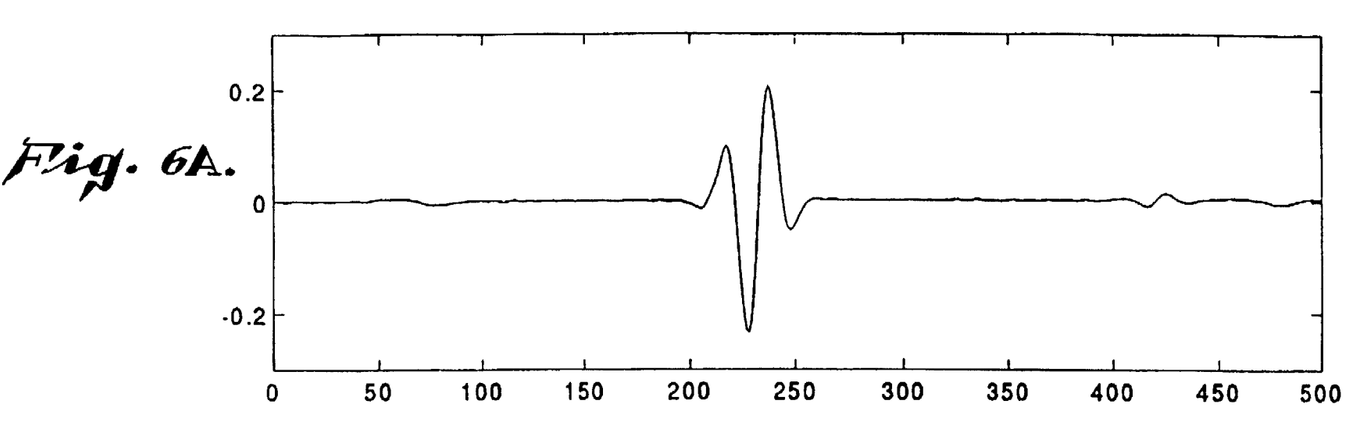
FIGS. 6A to 6E are representative electrogram morphologies processed in accordance with the pattern matching technique shown in FIG. 5.
Figure 6B:
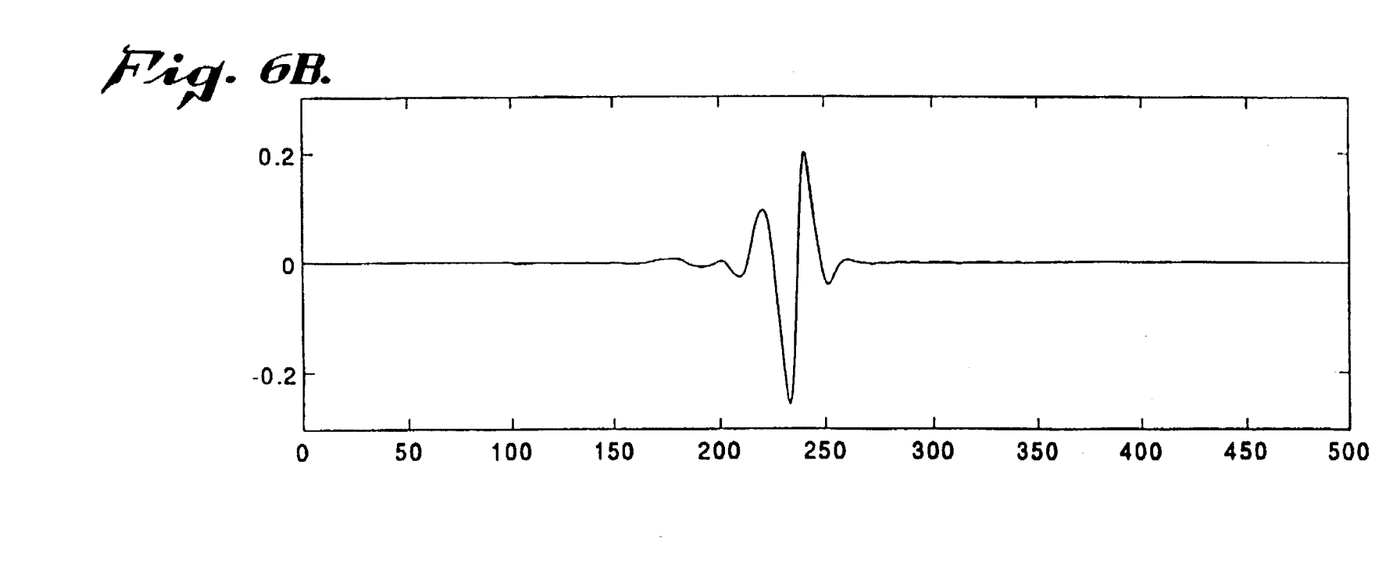
Figure 6C:
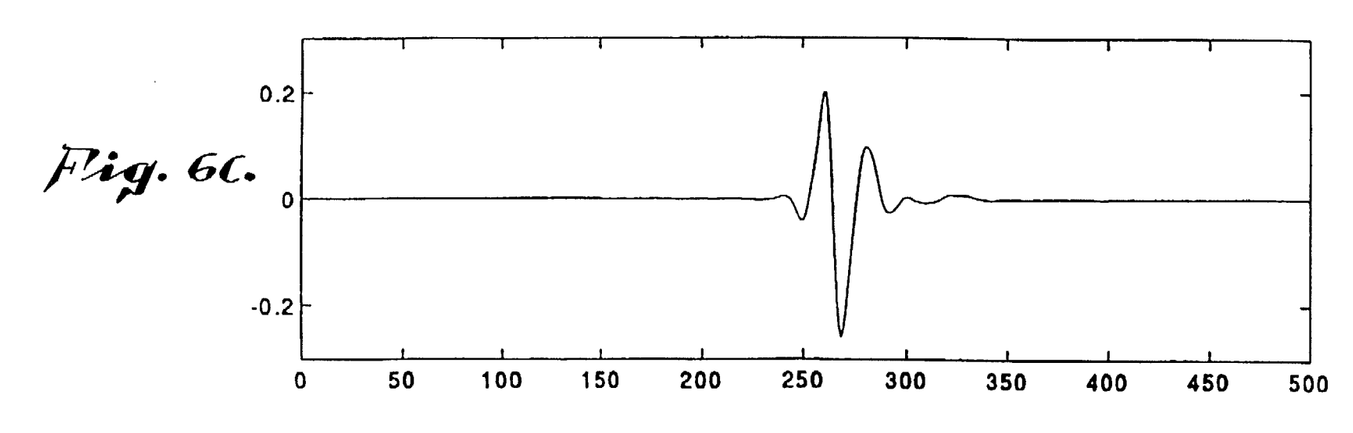
Figure 6D:
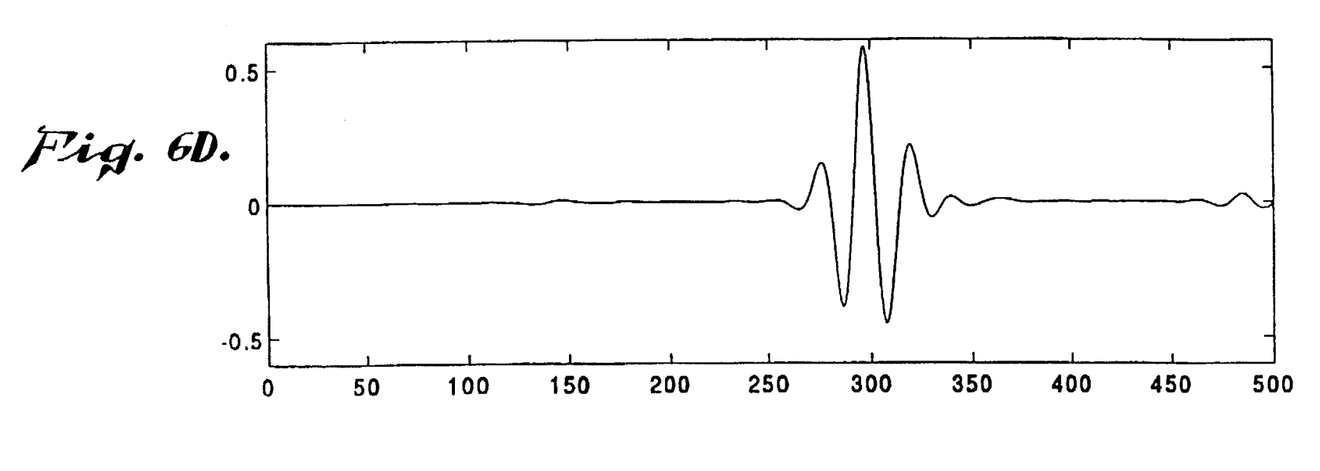
Figure 6E:
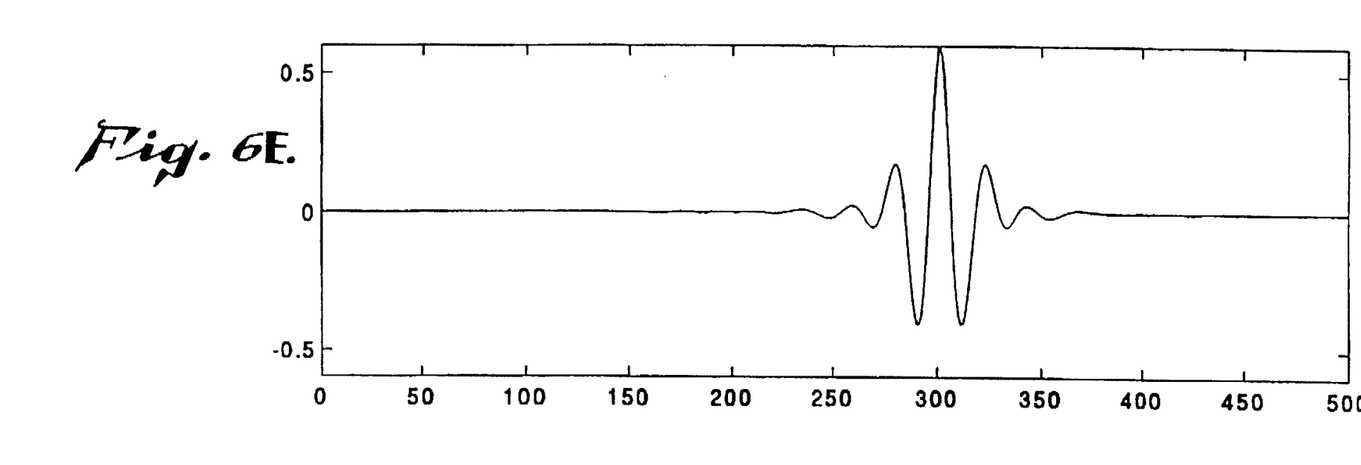

FIG. 5 diagrammatically shows a representative pattern matching technique. The pattern matching technique matched filters the template T(i) for each electrode E(i) using the same template flipped left to right with respect to time, Tflip(i), as coefficients of the matched filter. FIG. 6B shows a representative template T(i) for a given electrode E(i). FIG. 6C shows Tflip(i), which is the template T(i) (shown in FIG. 6B) flipped right to left. FIG. 6E shows a matched filtered output MT(i), which had T(i) (FIG. 6B) as input and Tflip(i) (FIG. 6C) for the same electrode E(i) as coefficients of the matched filter. As FIG. 6E shows, the matched filtered output MT(i) is, for the electrode E(i), a sequence of alternating maximums and minimums, with their values marking a first pattern employed by this technique.

The pattern matching technique also matched filters the paced electrogram P(i) for each electrode E(i) using an identical matched filter as the one described above. FIG. 6A shows a representative paced electrogram P(i) for the given electrode E(i). FIG. 6D shows the matched filtered output MP(i), using Tflip(i) shown in FIG. 6C as the matched filter coefficients. Like MT(i), the matched filtered output MP(i) is, for each electrode E(i), a sequence of alternating maximums and minimums, which are used to construct a second pattern.

The pattern matching technique detects the maximums and minimums for the matched filtered template outputs MT(i) and those of MP(i). The pattern matching technique places the maximums and minimums in two odd-length, L-sized model vectors, correspondingly, where L is the total number of local extremes of MT(i) and MP(i). The pattern matching technique computes the norm of the difference between the MP-pattern and the corresponding MT-pattern shifted by an amount, P, that varies from−(L-K) to (L-K), where K c L/2. The maximum number of comparisons for n electrodes will be n comparisons for each pacing electrode. Alternatively, one can shift the MP-patterns as just described, keeping the corresponding MT-patterns fixed. The largest excursions are placed in the centers of the template and paced vectors.

For example, assuming $$MT(i) = \{mt(i, 1), mt(i, 2), mt(i, 3)\},$$

and $$MP(i) + \{mp(i, 1 + p), mp(i, 2 + p), mp(i, 3 + p)\}, \text{ then}$$

$$norm_{(i, p)} = \|MT(i) - MP(i)\| \text{ or}$$

$$norm_{(i,p)} = \sqrt{\Sigma[mt(i, r) - mp(i, r + p)]^2}$$

where r=1 to 3 and p=−(L-K) to (L-K).

The minimum of the above is used as the matching coefficient for the sequence of norms ($M_{COEF(i)}$), i.e.:

$$M_{COEF(i)} = \min(norm_{i,p})$$

for p=−(L-K) to (L-K).

The minimum norms of the electrodes are averaged by an appropriate weighted average algorithm (as above discussed). This yields the overall matching factor $M_{PACE(j)}$ for each pacing electrode Ep(j), i.e.:

$$M_{PACE(j)} = \frac{\Sigma M_{COEF(i)}}{n}$$

Other representative matching techniques are described in copending U.S. patent application Ser. No. 08/390,559, filed Feb. 17, 1995, and entitled "Systems and Methods for Analyzing Biopotential Morphologies in Body Tissue."

In a preferred implementation, the host processor 52 sets a match target $N_{MATCH}$, which numerically establishes a matching factor $M_{PACE(j)}$ at which a high probability exists that the pacing electrode is close to a potential ablation site. In a preferred implementation, $N_{MATCH}$=0.8. When $M_{PACE(j)}$>$N_{MATCH}$, the host processor 52 deems the location of the pacing electrode Ep(j) to be close to a potential site for ablation. When this occurs (as FIG. 4 shows), the host processor 52 transmits a SITE signal to an associated output display device 54 (see FIG. 1). Through visual prompts, the display device 54 notifies the physician of the location of the pacing electrode Ep(j) and suggests that the location as a potential ablation site.

III. THE MULTI-PURPOSE STUNNING ABLATION PROBE

Figure 3:
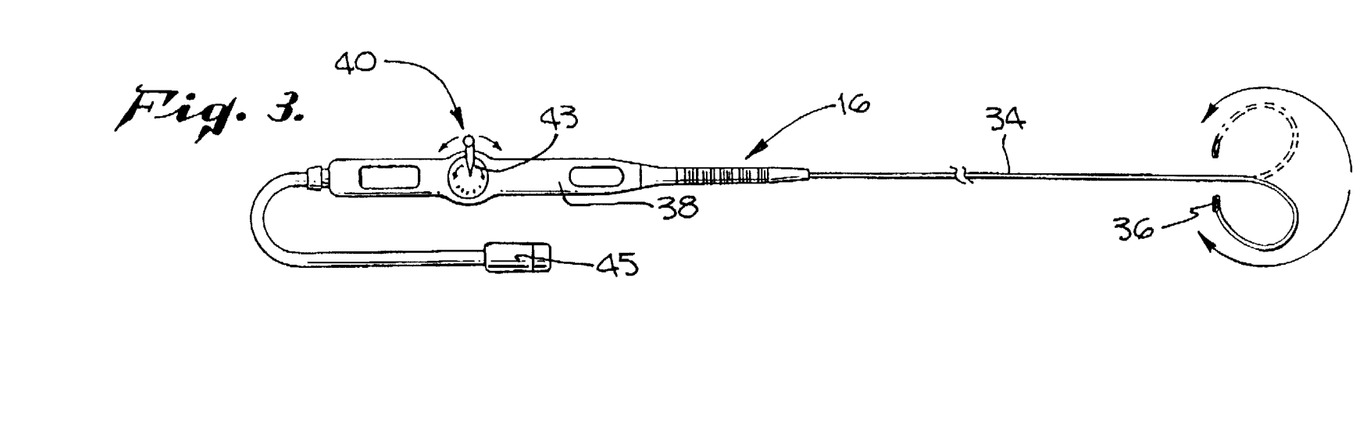
FIG. 3 is an enlarged view of an ablation probe usable in association with the system shown in FIG. 1.

The multi-purpose stunning-ablation probe 16 (see FIG. 3) includes a flexible catheter body 34 that carries one or more electrodes 36. For the sake of illustration, FIG. 3 shows a single electrode 36 carried at the distal tip of the catheter body 34. Of course, other configurations employing multiple electrodes are possible, as described in pending U.S. patent application Ser. No. 08/287,310, filed Aug. 8, 1994, entitled "Systems and Methods for Ablating Heart Tissue Using Multiple Electrode Elements."

A handle 38 is attached to the proximal end of the catheter body 34. The handle 38 and catheter body 34 carry a steering mechanism 40 for selectively bending or flexing the catheter body 34 along its length, as the arrows in FIG. 3 show.

The steering mechanism 40 can vary. For example, the steering mechanism can be as shown in U.S. Pat. No. 5,254,088, which is incorporated herein by reference.

A wire (not shown) electrically connected to the electrode 36 extends through the catheter body 34 into the handle 38, where it is electrically coupled to an external connector 45. The connector 45 connects the electrode 36 to a generator 46, which supplies electromagnetic radio frequency energy to the electrode 36. As used in this Specification, the term "radio frequency energy" refers to electrical energy with frequencies in the range of between about 10 kHz to about 3 GHz ($3 \times 10^9$ Hz). When operated in a uni-polar mode, an external patch electrode (not shown) constitutes the radio frequency energy return line. When operated in a bipolar mode, an electrode carried on the catheter body 34 constitutes the radio frequency energy return line.

It should be appreciated that other methodologies of ablating tissue can be used. For example, laser energy can be transmitted to ablate tissue. Fluids , like alcohol (ethanol), collagen, phenol, carbon dioxide, can also be injected into heart tissue for ablating it (see, e.g. Lesh et al. U.S. Pat. No. 5,385,148).

The generator 46 is operable through an associated switching element 80 (see FIG. 7) in two modes, called the stunning mode and the ablation mode.

A. The Stunning Mode

In the first mode, the generator 46 transmits via the switching element 80 one or more high voltage pulses through the electrode 36 into a local tissue region contacting or otherwise near the electrode 36. Each pulse has a prescribed waveform shape and duration that temporarily "stun" tissue in the local region without field stimulating tissue in regions farther away from the electrode 36.

The temporary stunning creates a likewise temporary electrical conduction block in the local region, rendering the tissue region electrically unresponsive to spontaneous or induced depolarization events. By observing the effect of the local conduction block upon ongoing cardiac events, the physician obtains diagnostic information helpful in locating and confirming potential tissue ablation sites.

By purposeful operation of the electrode 36 in the stunning mode in regions where the process controller 32 has assigned the larger overall matching factors $M_{PACE(j)}$, the system 10 is able to confirm and cross-check the location output of the process controller 32 to verify the location of a potentially efficacious ablation site before actually ablating tissue.

Figure 4B:
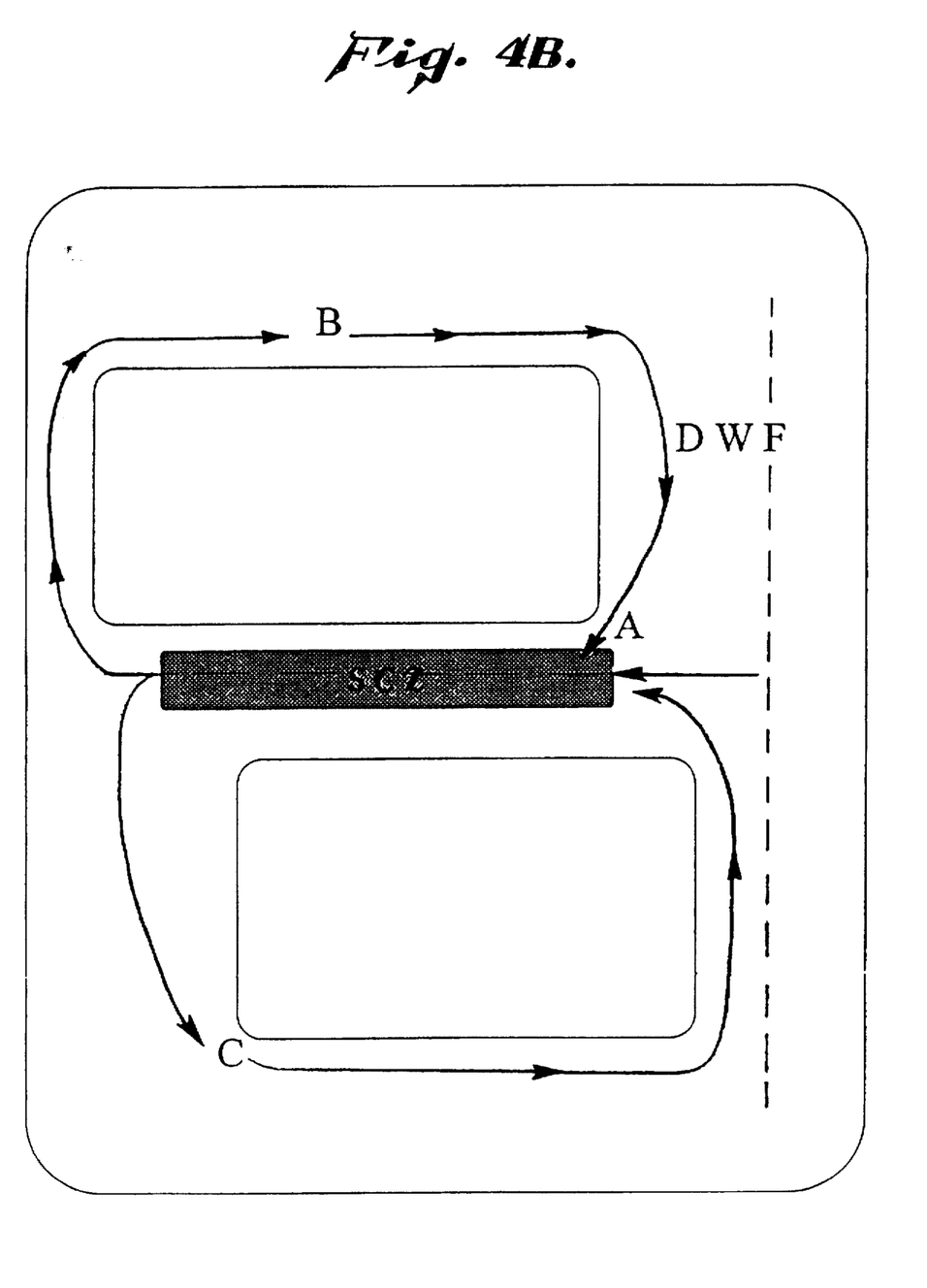
FIG. 4B is a schematic view of a slow conduction zone in myocardial tissue and the circular propagation patterns (called circus motion) it creates.

By way of example, the site appropriate for ablation to cure VT typically constitutes a slow conduction zone, designated SCZ in FIG. 4B. Depolarization wave fronts (designated DWF in FIG. 4B) entering the slow conduction zone SCZ (at site A in FIG. 4B) break into errant, circular propagation patterns (designated B and C in FIG. 4B), called "circus motion." The circus motions disrupt the normal depolarization patterns, thereby disrupting the normal contraction of heart tissue to cause the cardiac event.

The event-specific templates T(i) generated by the process controller 32 record these disrupted depolarization patterns. When a pacing signal is applied to a slow conduction zone, the pacing signal gets caught in the same circus motion (i.e., paths B and C in FIG. 4B) that triggers the targeted cardiac event. A large proportion of the associated pacing morphologies P(i) at the sensing electrodes E(i) will therefore match the associated event-specific templates P(i) recorded during the targeted cardiac event. This leads to a greater number of larger matching coefficients $M_{COEF(i)}$ and thus to a larger overall matching factor $M_{PACE(j)}$.

However, when a pacing signal is applied outside a slow conduction zone, the pacing signal does not get caught in the same circus motion. It propagates free of circus motion to induce a significantly different propagation pattern than the one recorded in the templates T(i). A large proportion of the pacing morphologies P(i) at the sensing electrodes E(i) therefore do not match the event-specific templates T(i). This leads to a smaller number of larger matching coefficients $M_{COEF(i)}$ and thus to a smaller overall matching factor $M_{PACE(j)}$.

This is why the overall matching factor $M_{PACE(j)}$ becomes larger the closer the pacing electrode Ep(j) is to the slow conduction zone, which is the potential ablation site. The difference in propagation patterns between pacing inside and outside a slow conduction zone is particularly pronounced during entrainment pacing. For this reason, entrainment pacing is preferred.

Ablating tissue in or close to the slow conduction zone (designated SCZ in FIG. 4B) prevents subsequent depolarization. The destroyed tissue is thereby "closed" as a possible path of propagation. Depolarization events bypass the ablated region and no longer become caught in circus motion. In this way, ablation can restore normal heart function in the treatment of VT.

In treating VT, the physician therefore places the electrode 36 in a located tissue region where the process controller 32 assigned a larger overall matching factor $M_{PACE(j)}$. The process controller 32 can include a homing module 70 to aid the physician in guiding the electrode 36 in the located region. Systems and methods for operating the homing module 70 are disclosed in copending patent application Ser. No. 08/320,301, filed Oct. 11, 1994, and entitled "Systems and Methods for Guiding Movable Electrode Elements Within Multiple Electrode Structures", which is incorporated herein by reference.

With the electrode 36 in position, and before transmitting ablation energy, the physician conditions the generator 46 through the switching element 80 for operation in the stunning mode. The physician also conditions the process controller 32 to induce the cardiac event to be treated, which in this example is VT, unless the cardiac event is otherwise spontaneously occurring. As the cardiac event occurs, the electrode 36 transmits one or more stunning pulses into the tissue region nearest to it. The stunning pulses are timed to the local electrogram to be transmitted when local depolarization occurs.

The waveform pattern, duration, and amplitude of the stunning pulses effective to stun an efficacious volume of myocardium can be empirically determined by in vivo or in vitro tests and/or computer modeling.

The character of the stunning pulse is expressed in terms of its waveform shape, its duration, and its amplitude. The duration and amplitude are selected so as to create a temporary electrical conduction block without damage to the tissue. For the purpose of this Specification, the term "temporary" refers to a time period less than about five minutes.

The duration of the pulse can vary from microseconds up to several seconds, depending upon the waveform (DC or AC) of the pulse, amplitude of the pulse, and the electrode configuration. There is a strength-duration relationship between pulse duration and amplitude, with somewhat higher voltages requiring shorter pulse durations to stun, but not kill, tissue. Short pulse durations not exceeding about 100 milliseconds are preferred.

The pulse amplitude, $S_{AMP}$, selected depends upon the voltage gradient, the configuration of the electrode 36, the depth of tissue penetration desired, and the impedance of the system 10, expressed as follows:

$$S_{AMP} = \left(\frac{S_V}{L}\right) \times \left(\frac{A}{\rho}\right) \times R$$

where:

the quantity $S_V/L$ represents the local voltage gradient. As a benchmark, DC voltage gradients of between about 70 volts/cm and 200 volts/cm that are about 10 milliseconds in duration, when delivered by defribillation catheters, have been shown to temporarily stun chicken embryo myocardial tissue in vitro, rendering it electrically unresponsive. The stunning in these instances extends about 1 cm from the electrode when a 800 volt (DC) shock is delivered. Higher voltage gradients increase the risk of killing myocardial tissue. The duration of unresponsiveness of stunned tissue varies from 1 to 60 seconds and more, depending upon the local voltage gradient. The effective volume of the local conduction block shrinks with time, as tissue exposed to lower voltage gradients at the edges of the stunned tissue volume recover faster than tissue exposed to higher voltage gradients at the center of the stunned tissue volume. See, e.g. Jones et al., "Microlesion Formation in Myocardial Cells by High Intensity Electric Field Stimulation," the American Physiological Society (1987), pp. H480–H486; Jones et al., "Determination of Safety Factor for Defibrillator Wave-forms in Cultured Cell Hearts," the American Physiological Society (1982), pp. H662–H670. Based upon the foregoing in vitro benchmarks, it is believed that a nominal voltage gradient of about 133 volts/cm can be safely selected.

A is the cross sectional area of the voltage gradient, which is assumed to be a spherical section with a radius, r, measured from the center of the electrode body to the tissue where stunning occurs. For example, for r=1 cm, the quantity A (assumed to be the area of a circle with radius, r, of 1 cm) is about 6 cm$^2$ (i.e., $2\pi r^2$). Relatively shallow lesions (about 5 mm), for which the radius, r, is relatively short, are effective in treating some arrhythmias. However, larger and deeper lesions (up to and exceeding 1 cm), for which the radius, r, are longer, are generally required when treating VT.

ρ is the resistivity of the tissue to be stunned. For an electrode exposed to both blood and myocardial tissue, ρ is believed to be about 200 Ohm.cm.

R is the impedance of the delivery system and electrode that transmits the pulse.

Larger electrodes (greater than about 4 mm) require somewhat lower voltages to achieve the same stunning effect. This is primarily because of decreased losses in near-field tissue because of decreased current densities at the surface of larger electrodes.

The waveform shape and period is selected so that the pulse will not field stimulate tissue at sites distant from the electrode 36. A stunning pulse that causes far field stimulation can cardiovert (i.e., stop) the entire cardiac event for reasons other than a temporary, localized conduction block. Cardioversion therefore can overshadow the desired, more discrete specificity of the stunning effect. The character of the stunning pulse is selected to induce only a temporary conduction block in a discrete, relatively small volume of tissue generally equal to the volume of tissue to be ablated. A biphasic or uniphasic square wave (DC) transmitted for a short duration (about 100 microseconds) will achieve this effect. A sinusoidal (AC) signal at frequencies above about 10 kHz for durations of about 100 milliseconds will also achieve this effect. The DC pulse or short duration AC signal can be transmitted either unipolar (as the illustrated embodiment shows) or in a bipolar mode.

Based upon the foregoing considerations, for an electrode diameter of about 4 mm, a radio frequency pulse having an amplitude of about 100 volts (at 500 kHz) and a duration of about 100 milliseconds will stun tissue to a depth of about 5 mm (which is sufficient when treating supra-ventricular tachycardia (SVT)). With the same 4 mm electrode, a larger pulse amplitude of about 400 volts (at 500 kHz) at a duration of about 100 milliseconds will stun tissue to a deeper depth of about 1 cm (which is required for treating VT). Taking typical electrode configurations and typical ranges of stunning depths into account, the radio frequency pulse amplitude (at 500 kHz) will range from about 100 volts up to about 800 volts (at 500 kHz), with durations less than about 100 milliseconds.

When the selected pulse stuns tissue laying in the ablation-targeted slow conduction zone, the temporarily rendering of this zone electrically unresponsive will temporarily interrupt the cardiac episode (VT in this illustration), just as ablation in the zone will permanently stop the cardiac episode. In this respect, stunning serves as a temporary preview of the intended permanent ablation effect.

Should the stunning interrupt the cardiac episode, the physician waits for the temporary conduction block to resolve and VT to reappear. Typically, this will take about 30 seconds. The physician then preferably repeats the transmission of one or more selected stunning pulses to confirm the interruption of VT, thereby confirming the presence of the ablation-targeted slow conduction zone near the electrode 36.

If VT continues uninterrupted despite the transmission of one or more stunning pulses, the physician knows that the stunned tissue does not include the ablation-targeted slow conduction zone. In this circumstance, the physician repositions the electrode 36 to a different location geometrically near to the last stunned site. The physician transmits one or more stunning pulses into tissue at the new site and observes the effect upon the spontaneous or induced VT episode.

The physician repeats these steps, operating the electrode 36 in the stunning mode in the vicinity of all tissue regions the process controller 34 assigns a high overall matching factor $M_{PACE(j)}$, until a site where stunning consistently interrupts VT is located.

When the stunning pulse or pulses repeatedly interrupt the spontaneous or induced VT episode at a given site, the physician targets the site for ablation. The physician can titrate the volume of tissue comprising the slow conduction zone by varying the amplitude of the stunning pulse and observing the effect upon VT-interruption.

Having targeted the ablation site and titrated its volume, the physician, without altering the position of the electrode 36, conditions the generator 46 through the switching element 80 for operation in the second or ablation mode.

In an alternative embodiment, the physician stuns the selected local region and then operates the process controller 34 to induce the desired cardiac event. In this embodiment, the physician observes whether stunning the selected local region suppresses the desired cardiac event. When stunning a given selected region consistently suppresses the desired cardiac event, which in the absence of stunning occurs, the physician targets the given region for ablation.

It should be appreciated that the use of high voltage stunning can be carried out in association with conventional electrocardiogram analysis, without the use of a multiple electrode mapping probe or the template matching technique described above. The use of a multiple electrode mapping probe and associated electrocardiogram matching techniques is preferred, as they provide a more accurate indication where stunning should be applied than conventional techniques.

It should also be appreciated that the stunning pulses can alternatively comprise DC or AC energy transmitted by the electrode 36 from a source separate from the generator 46.

B. The Ablation Mode

In the second mode, the generator 46 transmits lower voltage radio frequency energy through the same electrode 36 into a selected tissue region near the electrode 36. The radio frequency energy has a waveform shape and duration that electrically heats and kills tissue in the selected region. Typically, when used for cardiac ablation, the generator 46 is conditioned to deliver up to 150 watts of power for about 10 to 120 seconds at a radio frequency of 500 kHz. By destroying the tissue, the radio frequency energy forms a permanent electrical conduction block in the tissue region.

Figure 7:
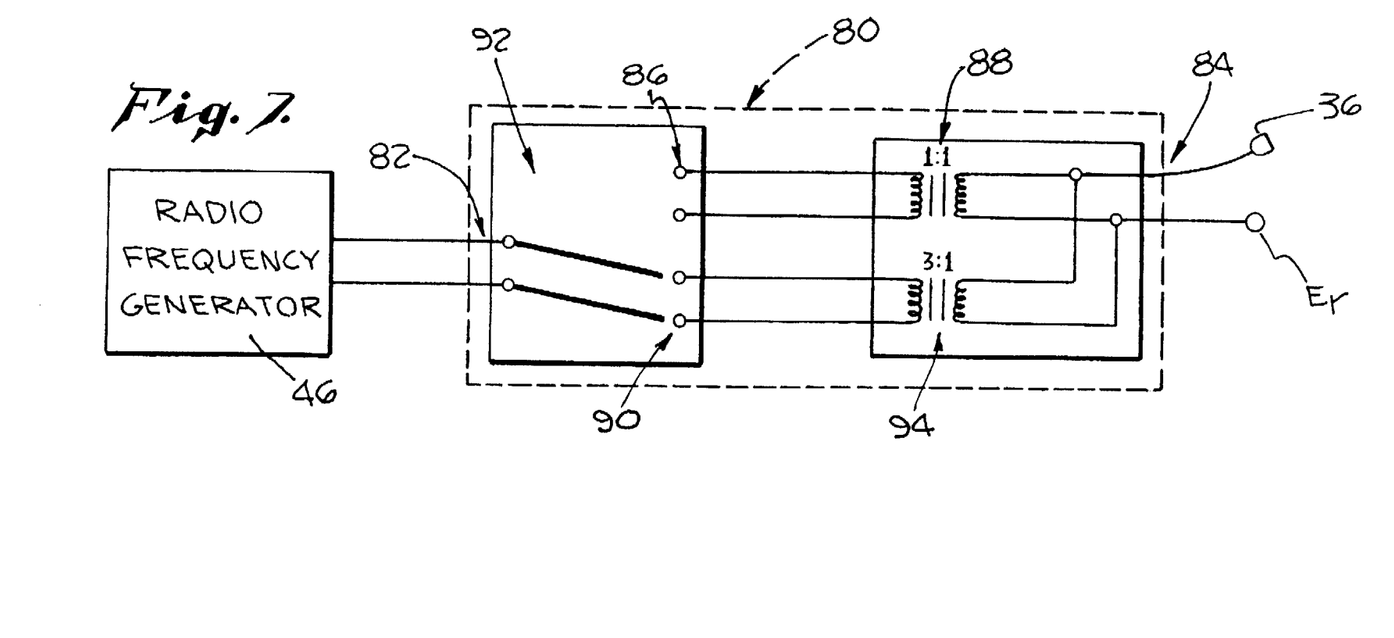
FIG. 7 is a diagrammatic view of a representative switching element used in association with the radio frequency energy generator for switching between stunning mode and ablation mode.

FIG. 7 shows a representative implementation for the switching element 80 associated with the generator 46 to change operation between the stunning mode and the ablation mode. In this embodiment, the switching element input 82 (comprising supply and return lines) is coupled to the generator 46, which delivers radio frequency energy (500 kHz) at a prescribed energy input level suitable for stunning, as previously described. The switching element output 84 (also comprising supply and return lines) is coupled to the transmitting electrode 36 and to the return line electrode, designated $E_r$ in FIG. 7.

The switching element 80 includes an electronic switch 92 defining a first switch path 86 and a second switch path 90.

The first switch path 86 conditions the generator 46 for operation in the stunning mode. The first switch path 86 includes a first isolation transformer 88. The isolation transformer 88, shown in FIG. 7 as a 1:1 transformer, directs the stunning energy through the electrode 36 without amplitude modification for stunning tissue in the manner described. In the stunning mode, the electronic switch 92 transmits stunning energy through the first switch path 86 in short cycle intervals to deliver the energy in preset stunning pulses, as already described.

The switching element 80 also includes a second switch path 90, which conditions the generator 46 for operation in the ablation mode. The second switch path 90 includes a second step-down isolation transformer 94, which is shown for the purpose of illustration having a step-down ratio of 3:1. The transformer 94 decreases the amplitude of the energy transmitted to the electrode 36 to lower levels suitable for ablating tissue, as already described. In the ablation mode, the electronic switch 92 transmits energy through the second switch path 90 for longer cycle intervals conducive to tissue ablation, as also already described.

C. Roving Pacing Mode

In an alternative embodiment, the multi-purpose stunning-ablation probe 16 can also be conditioned for use by the process controller 34 as a roving pacing probe, usable in tandem with the basket structure 20 to generate and verify the location output during the above described sampling and matching modes.

In this arrangement, the probe 16 is deployed in the heart region 12 while the multiple electrode structure 20 occupies the region 12. In this mode, the electrode 36 is electrically coupled to the pacing module 48 (as shown in phantom lines in FIG. 1) to emit pacing signals.

In use, once the process controller 32 generates the output location or locations using the electrodes 24 to pace the heart, the physician positions the probe 16 within the localized region near the output location electrode or electrodes 24. As above described, the process controller 32 preferably includes the homing module 70 to aid the physician in guiding the probe 16 in the localized region within the structure 20.

The process controller 32 conditions the pacing module 48 to emit pacing signals through the electrode 36 to pace the heart in the localized region, while the electrodes 24 record the resulting electrograms. By pacing this localized region with the probe 16, while comparing the paced electrograms with the templates, the process controller 32 provides the capability of pacing and comparing at any location within the structure 20. In this way, the process controller 32 generates as output a location indicator that locates a site as close to a potential ablation site as possible.

Due to the often convoluted and complex contours of the inside surface of the heart, the basket structure 20 cannot contact the entire wall of a given heart chamber. The system 10 therefore can deploy the probe 16 outside the structure 20 to pace the heart in those wall regions not in contact with the electrodes 24. The probe 16 can also be deployed while the basket structure 20 occupies the region 12 to pace the heart in a different region or chamber. In either situation, the electrodes 24 on the structure 20 record the resulting paced electrograms for comparison by the process controller 32 to the templates. The process controller 32 is thus able to generate an output identifying a location close to a potential ablation site, even when the site lies outside the structure 20 or outside the chamber that the structure 20 occupies.

D. Electrophysiologic Diagnosis Mode

The generator 46 can be operated in the stunning mode in association with the probe 16 to conduct diagnostic electrophysiological testing of myocardial tissue, in place of or in tandem with the mapping probe 14.

In this mode of operation, the physician conditions the generator 46 to transmit through the electrode 36 an electrical energy pulse, as previously described, which temporarily renders a zone of myocardial tissue electrically unresponsive. By sensing an electrophysiological effect due to the transmitted pulse, the physician can diagnose the cause of cardiac events.

For example, by temporarily rendering zones of myocardial tissue electrically unresponsive using an electrical energy pulse, and sensing the resulting electrophysiological effect, the physician can, without using the mapping probe 14, locate sites of automaticity, also called pacemaker sites, where arrhythmia originates. Likewise, the physician can, without using the mapping probe 14, locate the path or paths that maintain arrhythmia, previously referred to as the areas of slow conduction. Furthermore, by temporarily rendering zones of myocardial tissue electrically unresponsive using the electrical energy pulse, the physician can selectively alter the conduction properties of the heart within the localized zone without otherwise changing electrophysiological properties outside the zone. For example, the physician can create a temporary AV block by operating the generator 46 in the stunning mode, as previously described.

Based at least in part upon these diagnostic tests conducted in the stunning mode, the physician can proceed to altering an electrophysiological property of myocardial tissue in or near a diagnosed zone. For example, the physician can alter the electrophysiological property by ablating tissue in or near the diagnosed zone, as above described, using radio frequency electrical energy, or laser light energy, or an ablation fluid. The physician can also mediate the diagnosed cardiac disorder without ablating tissue, using drugs such as quinidine, digitalis, and lidocaine.

Various features of the invention are set forth in the following claims.

I claim:

1. A method for conducting diagnostic electrophysiological testing of myocardial tissue comprising the steps of
    transmitting an electrical energy pulse that temporarily renders a zone of myocardial tissue electrically unresponsive for at least one second, and
    sensing an electrophysiological effect due to the transmitted pulse.

2. A method according to claim 1
    and further including the step of altering an electrophysiological property of myocardial tissue in or near the zone based, at least in part, upon the sensed electrophysiological effect.

3. A method according to claim 2
    wherein the step of altering the electrophysiological property includes ablating myocardial tissue in or near the zone.

4. A method according to claim 3
    wherein, in the step of ablating myocardial tissue, electrical energy is used.

5. A method according to claim 3
    wherein, in the step of ablating myocardial tissue, light energy is used.

6. A method according to claim 2 wherein the step of altering the electrophysiological property includes injecting chemical into the myocardial tissue.

7. A method according to claim 1 wherein the transmitted electrical energy pulse comprises a DC waveform.

8. A method according to claim 1 wherein the transmitted electrical energy pulse comprises an AC waveform.

9. A method according to claim 1 wherein the transmitted electrical energy pulse comprises a radio frequency energy waveform.

10. A method according to claim 9 and further including the step of altering an electrophysiological property of myocardial tissue in or near the zone based, at least in part, upon the sensed electrophysiological effect using a radio frequency waveform to ablate myocardial tissue.

11. A method for ablating myocardial tissue comprising the steps of transmitting an electrical energy pulse that temporarily renders myocardial tissue electrically unresponsive for at least one second, sensing an electrophysiological effect due to the transmitted pulse, and ablating the myocardial tissue based, at least in part, upon the sensed electrophysiological effect.

12. A method according to claim 11 wherein the transmitted electrical energy pulse comprises a DC waveform.

13. A method according to claim 11 wherein the transmitted electrical energy pulse comprises an AC waveform.

14. A method according to claim 11 wherein the transmitted electrical energy pulse comprises a radio frequency energy waveform.

15. A method for ablating myocardial tissue comprising the steps of transmitting a radio frequency energy pulse to temporarily rendered myocardial tissue electrically unresponsive for at least one second, sensing an electrophysiological effect due to the transmitted radio frequency energy pulse, and ablating the myocardial tissue based, at least in part, upon the sensed electrophysiological effect.

16. A method for ablating myocardial tissue comprising the steps of transmitting a radio frequency energy pulse into myocardial tissue to temporarily render the myocardial tissue electrically unresponsive for at least one second, sensing an electrophysiological effect due to the transmitted pulse, and transmitting radio frequency energy to ablate the myocardial tissue based at least in part, upon the sensed electrophysiological effect.

17. A method for ablating heart tissue comprising the steps of sensing at least one electrical event in a region of myocardial tissue, transmitting into an area of the region an electrical energy pulse that temporarily renders myocardial tissue in the area electrically unresponsive for at least one second, sensing a change in the electrical event while myocardial tissue in the area is electrically unresponsive, and ablating myocardial tissue in or near the area.

18. A method according to claim 17 wherein the transmitted electrical energy pulse comprises a DC waveform.

19. A method according to claim 17 wherein the transmitted electrical energy pulse comprises an AC waveform.

20. A method according to claim 17 wherein the transmitted electrical energy pulse comprises a radio frequency energy waveform.

21. A system for conducting diagnostic electrophysiological testing of myocardial tissue comprising an electrode, a body supporting the electrode proximate to a region of myocardial tissue, a first element coupled to the electrode including means for transmitting through the electrode an electrical energy pulse that temporarily renders a zone of myocardial tissue electrically unresponsive for at least one second, and a second element including means supported proximate to the region of myocardial tissue for sensing an electrophysiological effect due to the transmitted pulse and providing an output.

22. A system according to claim 21, wherein the first element includes operative means supported proximate to the zone for altering an electrophysiological property of myocardial tissue in or near the zone based, at least in part, upon the sensed electrophysiological effect.

23. A system according to claim 22 wherein the operative means alters the electrophysiological property by ablating myocardial tissue in or near the zone.

24. A system according to claim 23 wherein the operative means transmits electrical energy to ablate myocardial tissue.

25. A system according to claim 23 wherein the operative means transmits light energy to ablate myocardial tissue.

26. A system according to claim 22 wherein the operative means injects chemical into the myocardial tissue.

27. A system according to claim 21 wherein the means of first element transmits an electrical energy pulse comprising a DC waveform.

28. A system according to claim 21 wherein the means of first element transmits an electrical energy pulse comprising an AC waveform.

29. A system according to claim 21 wherein the means of first element transmits an electrical energy pulse comprising a radio frequency energy waveform.

30. A system according to claim 21, wherein the first element includes means supported proximate to the zone for altering an electrophysiological property of myocardial tissue in or near the zone based, at least in part, upon the sensed electrophysiological effect using a radio frequency waveform to ablate myocardial tissue.

31. A system for ablating myocardial tissue comprising an electrode, a body supporting the electrode in operative association with a region of myocardial tissue, an element coupled to the electrode including transmitting means for transmitting through the electrode an electrical energy pulse that temporarily renders myocardial tissue electrically unresponsive for at least one second, and ablation means, operably connected to the body, supported proximal to the myocardial tissue region for ablating the myocardial tissue region.

32. A system according to claim 31 wherein the transmitting means transmits an electrical energy pulse comprising a DC waveform.

33. A system according to claim 32 wherein the ablation means transmits radio frequency energy to ablate myocardial tissue.

34. A system according to claim 31 wherein the transmitting means transmits an electrical energy pulse comprising an AC waveform.

35. A system according to claim 34 wherein the ablation means transmits radio frequency energy to ablate myocardial tissue.

36. A system according to claim 31 wherein the transmitting means transmits an electrical energy pulse comprising radio frequency energy.

37. A system according to claim 36 wherein the ablation means transmits radio frequency energy to ablate myocardial tissue.

38. A system according to claim 31 wherein the ablation means transmits radio frequency energy to ablate myocardial tissue.

39. A system for ablating myocardial tissue comprising
an electrode,
a body supporting the electrode proximal to a region of myocardial tissue,
a first element coupled to the electrode including means for transmitting through the electrode an electrical energy pulse that temporarily renders myocardial tissue electrically unresponsive for at least one second, and
a second element coupled to the electrode including means for transmitting electrical energy through the electrode to ablate the myocardial tissue region.

40. A system for ablating myocardial tissue comprising
an electrode,
a body supporting the electrode proximal to a region of myocardial tissue,
a generator of radio frequency energy coupled to the electrode and operable in a first mode and in a second mode, and
a controller conditioning the generator for operation in the first mode, during which the generator generates for transmission by the electrode at least one pulse of radio frequency energy that creates a temporary electrical conduction block in myocardial tissue for at least one second, the controller also conditioning the generator for operation in the second mode, during which the generator generates for transmission by the electrode radio frequency energy that ablates myocardial tissue.

41. An electrical energy generating device adapted to be coupled to an electrode comprising
first means for, when activated, generating for transmission by the electrode an electrical energy pulse that temporarily renders myocardial tissue electrically unresponsive for at least one second,
second means for, when activated, generating for transmission by the electrode electrical energy to ablate myocardial tissue, and
a switch to select for activation either the first means or the second means.

42. A device according to claim 41 wherein the electrical energy pulse generated by the first means comprises a DC waveform.

43. A device according to claim 42 wherein the electrical energy generated by the second means comprises radio frequency energy.

44. A device according to claim 41 wherein the electrical energy pulse generated by the first means comprises an AC waveform.

45. A device according to claim 44 wherein the electrical energy generated by the second means comprises radio frequency energy.

46. A device according to claim 41 wherein the electrical energy pulse generated by the first means comprises a radio frequency energy waveform.

47. A device according to claim 46 wherein the electrical energy generated by the second means comprises radio frequency energy.

48. A device according to claim 41 wherein the electrical energy generated by the second means comprises radio frequency energy.

49. A method of treating myocardial tissue, comprising the steps of:
transmitting an electrical energy pulse that temporarily renders a zone of myocardial tissue electrically unresponsive without propagating a depolarization; and
sensing an electrophysiological effect due to the transmitted pulse.

50. A method as claimed in claim 49, further comprising the step of:
altering an electrophysiological property of the myocardial tissue in or near the zone, based at least in part, upon the sensed electrophysiological effect.

51. A method as claimed in claim 50, wherein the step of altering an electrophysiological property comprises ablating myocardial tissue in or near the zone.

52. A method as claimed in claim 50, wherein the step of altering an electrophysiological property comprises transmitting a radio frequency energy pulse to the myocardial tissue in or near the zone.

53. A method as claimed in claim 49, wherein the step of transmitting an electrical energy pulse comprises transmitting a radio frequency energy pulse.

54. A method as claimed in claim 49, further comprising the step of:
sensing a change in the electrical event while myocardial tissue in the area is electrically unresponsive.

55. An apparatus for use proximate to a region myocardial tissue, comprising:
an electrode;
first means for transmitting an electrical energy pulse through the electrode that temporarily renders a zone of myocardial tissue electrically unresponsive without propagating a depolarization; and
second means for sensing an electrophysiological effect in the region of myocardial tissue due to the transmitted pulse and providing an output.

56. An apparatus as claimed in claim 55, wherein the first means comprises means for transmitting radio frequency energy.

57. An apparatus as claimed in claim 55, further comprising:
third means for altering an electrophysiological property of the myocardial tissue in or near the zone.

58. An apparatus as claimed in claim 55, further comprising:
third means for ablating myocardial tissue in or near the zone.

* * * * *